United States Patent [19]
Paul

[11] Patent Number: 4,740,475
[45] Date of Patent: Apr. 26, 1988

[54] INTEGRAL SUBSTANCE DETECTION DEVICE AND METHOD

[75] Inventor: Philip C. Paul, Denver, Colo.

[73] Assignee: Medi-Scan, Inc., Denver, Colo.

[21] Appl. No.: 845,348

[22] Filed: Mar. 28, 1986

[51] Int. Cl.⁴ ............................................. G01N 31/22
[52] U.S. Cl. ........................................ 436/165; 422/58; 422/59; 422/61; 422/85; 422/86; 436/132; 436/167
[58] Field of Search ....................................... 422/56–59, 422/61, 86, 88, 68, 85; 436/165, 167, 168, 169, 132

[56] References Cited

U.S. PATENT DOCUMENTS

| | | | |
|---|---|---|---|
| 3,009,786 | 11/1961 | Luckey | 436/132 X |
| 3,022,141 | 2/1962 | Grosskopf | 422/86 X |
| 3,033,655 | 5/1962 | Grosskopf | 422/86 |
| 3,100,692 | 8/1963 | Wachter | 422/86 |
| 4,300,910 | 11/1981 | Pannwitz | 422/60 X |

*Primary Examiner*—Barry S. Richman
*Assistant Examiner*—Michael S. Gzybowski
*Attorney, Agent, or Firm*—Lee G. Meyer

[57] ABSTRACT

A disposable, self-contained, light weight integral device for detecting, by means of activating an indicator, the presence of a predetermined substance in a sample fluid which is introduced into a test chamber. The device has a deformable housing which forms a test chamber for interacting the indicator material with the sample fluid, wherein a rupturable vessel of reagent is contained adjacent the test chamber, which vessel can be ruptured by application of a predetermined pressure through the walls of the deformable housing. Upon rupturing the vessel, the contents thereof are exposed to the sample fluid introduced into the chamber. In the presence of the predetermined substance in the sample fluid, the indicator undergoes the indicated change. The device can contain more than one vessel and a receptacle. One or more of the vessels can contain more than one indicator substance.

10 Claims, 2 Drawing Sheets

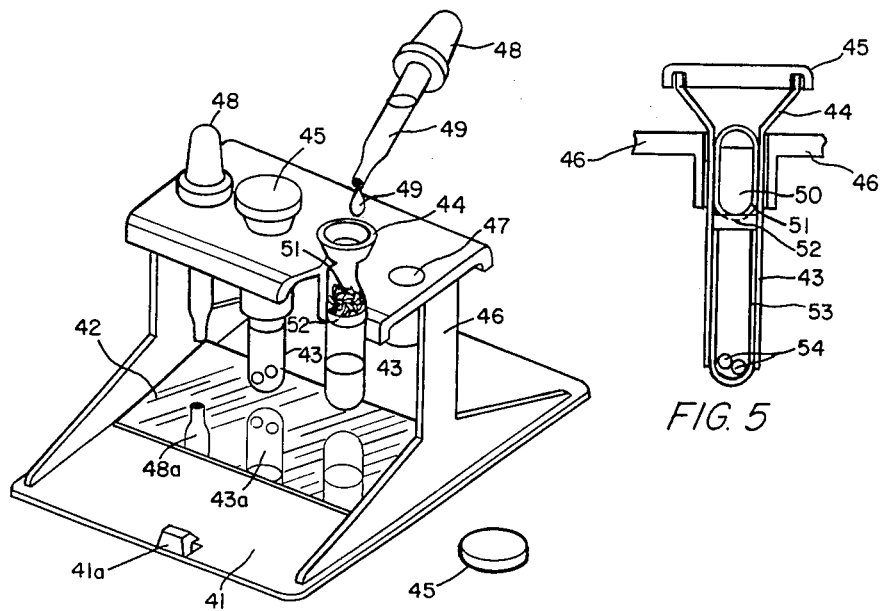
FIG. 4
FIG. 5
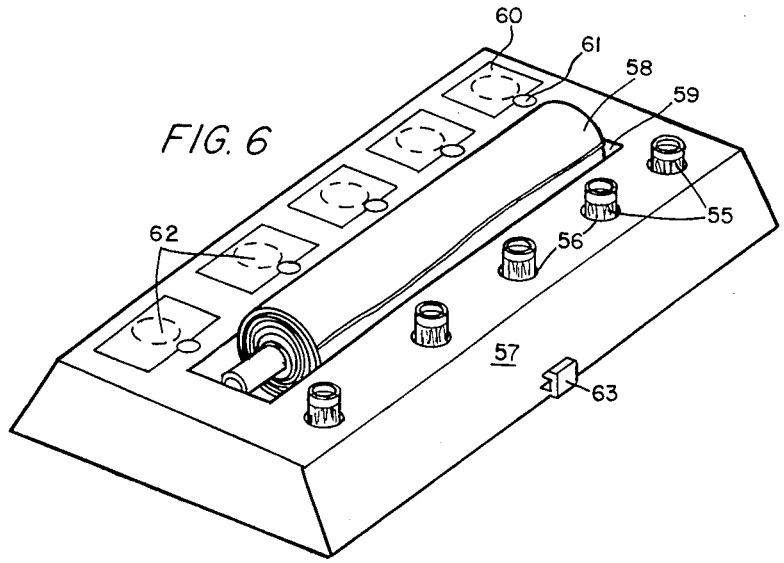
FIG. 6

INTEGRAL SUBSTANCE DETECTION DEVICE AND METHOD

DESCRIPTION

1. Technical Field

This invention relates to integral, disposable, field usable units for detecting the presence of substances in test fluids by use of indicator chemistry. More specifically, this invention relates to an easy-to-use, reliable, disposable device as well as a method for efficiently detecting the presence of a particular substance in human fluids such as blood, breath, saliva, perspiration, or urine.

2. Background Art

In today's medical world there is a need for sanitary, safe, easy-to-use, disposable detectors for use in connection with a myriad of medical tests designed to detect particular substances in the blood, breath, saliva, perspiration or urine. Alcohol consumption levels, for example, can be indicated by the presence of specific substances in the breath. Likewise, sugar levels in the urine can indicate the possible presence of diabetes, etc.

Many elaborate devices have been used in hospitals, clinics and other institutions to detect such substances. Many of these devices, although supposedly portable or mobile, involve large or bulky electrically driven equipment which may be difficult to calibrate and must be used by trained personnel in order to validate the results.

As an answer to these unwieldy devices, indicator reagents or materials and indicators of various types have been developed. The most common are chemical indicators which react in a certain prescribed manner in the presence of the substance being tested for. The problem associated with using chemical indicators is that of "freshness". These substances tend to deteriorate when exposed to the elements prior to use. Thus, these devices have heretofore had to be handled and stored carefully. Absence of chemistry freshness creates a potential of inaccurate results which has lead to a questioning of the reliability of these types of tests in general.

The ease of use of indicator chemistry for substance detection has led to the search for a method of insuring the freshness and integrity of the indicator chemistry so as to increase the accuracy and reliability of the tests. Specifically, there has been an attempt to hermetically seal or otherwise isolate the indicator chemistry to insure freshness upon use. Various units and cartridges contain plugs and seals to assure indicator reagent chemistry freshness have been developed. These are, for the most part, complicated and/or unwieldy. For example, U.S. Pat. No. 3,437,449 issued to M. J. Luckey teaches a blood alcohol measurement apparatus made up of a tube with both ends closed by removable polyethylene plugs. Centered within the tube are a series of substantially dry plugs of reagent impregnated with silica gel. The impregnated plugs are separated by plugs of inert granules, i.e., glass grit. The plugs are centered on o-rings and glass fiber. Adjacent the polyethylene plugs are small amounts of silica gel which absorb any sulfur dioxide given off by a reagent.

U.S. Pat. No. 3,459,508 issued to L. Miczka teaches the use of a reagent which changes color when in contact with alcohol and a serially positioned, moisture-responsive indicator agent which changes color when in contact with water. A change of color in the moisture-responsive indicator indicates that a predetermined volume of exhaled air has passed through the tube and through the alcohol test reagent. The moisture indicator is cobalt nitrate or material with equivalent characteristics. The alcohol test reagent suggested is permanganate or chromotosulphuric acid in granular form.

U.S. Pat. No. 4,329,318 issued to A. LeGrouyellac et al. teaches alcohol test capsules which are an improvement on the previously manufactured sealed glass ampules containing an indicator reagent. The device provides a gas or liquid test capsule of plastic. In use, the two ends of the plastic capsule are cut or broken off. The plastic tubes contain asperities which create a gas flow turbulence and improved penetration of test fluids into the reagent.

U.S. Pat. No. 4,080,170 issued to R. F. Borkenstein teaches a cartridge which uses calcium sulfate as an adsorban for alcohol. The adsorbant is positioned within the cartridge by spring loaded filter paper. The calcium sulfate is subsequently assayed by a test instrument to determine the amount of adsorbed alcohol.

Additionally, different types of closed glass tubes have been used. The Alcotest kit marketed by National Draeger, Inc., Pittsburgh, Pa., USA, utilized relatively thick-walled glass tubes which are fused to form tips on ends and which contain reagents for detecting alcohol, which reagents are centered by metal screen positioners. In use, the tips are broken off, a mouthpiece is placed on one end and a breath volume bag on the other. The subject to be tested then exhales through the assembly.

In all of the above prior art devices, the use of the device requires complicated instructions, breaking of exposed glass tubes, replacement of plugs and the like. Use of these devices ranges from cumbersome to dangerous (eg., exposed broken glass vials, etc.).

A single piece, disposable, substance detecting device which is easy to use and maintains chemistry freshness would be desirable.

DISCLOSURE OF THE INVENTION

An integral, completely disposable, on-the-spot, field usable, lightweight device capable of transport in a pocket or small container which maintains chemistry freshness has been discovered. In accordance with the instant invention, a portable, disposable, field substance detection device comprises at least one rupturable sealed vessel or vial which contains encapsulated therein an indicator reagent, which vessel is enclosed within a deformable housing having a test chamber to form a receptacle unit for testing fluids. The unit has at least one opening which communicates between the test chamber and the ambient environment for introducing substances into the chamber for testing. To activate the device, i.e. expose the indicator material, pressure is exerted through the deformable housing to rupture the sealed vessel encased therein, thus exposing the indicator reagent. The fluid to be tested (which may be a liquid or a gas) is introduced through the opening into the testing chamber where it intermingles with the indicator material to detect the indicated substance. In accordance with one embodiment, the carrier fluid is a gas and the test chamber communicates at both ends with ambient environment. In another embodiment, the carrier fluid is a liquid and the test chamber is adapted to receive the introduced fluid to be tested for the indicated substance.

In accordance with a further aspect of the instant invention, a plurality of rupturable sealed vessels or vials are contained within the deformable housing. Each vessel contains one or more indicator materials which are activated upon intermingling of the materials.

BRIEF DESCRIPTION OF THE DRAWINGS

FIG. 4 shows another embodiment of the instant invention for testing liquids.

FIG. 5 shows yet another embodiment of a fluid analysis kit.

FIG. 6 shows a breath analysis test kit.

DESCRIPTION OF THE INVENTION

Figure 1:
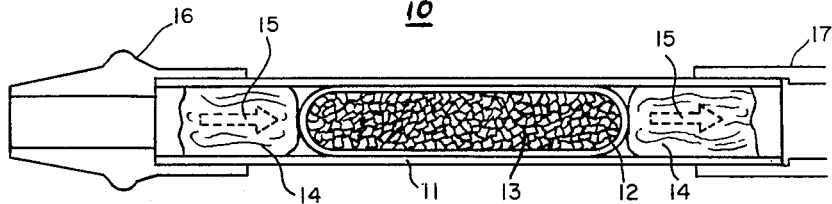
FIG. 1 shows a cutaway view of the test device of the instant invention adapted for detecting substances in a gaseous carrier fluid, such as alcohol in the breath.

As shown in FIG. 1, a testing unit 10 for detecting substances such as alcohol in the breath has a transparent, deformable housing or casing wall which forms a receptacle for a sealed, indicator-containing rupturable capsule or vial 12. Vial 12 contains an indicator 13 such as potassium dichromate. A porous retainer means 14 positions the vessel 12 within the deformable housing wall. Directional arrow 15 indicates the desired direction of the flow of exhaled breath (test fluid) through deformable housing 11 and through the test chamber. Mouthpiece 16, adapted to fit over the input end of the deformable housing 11 and the input tube 17 of a breath volume measuring bag (not shown) is fitted on the exit end of the deformable housing 11.

In operation, the unit 10 as shown in FIG. 1, is positioned between the fingers of the person administering the test such that suitable pressure is continuously exerted on the deformable housing 11 proximate the rupturable vessel 12 to rupture vessel 12, thus releasing indicator material 13 into the test chamber. The mouthpiece 16 is then attached along with the breath volume measuring bag (not shown). The subject then exhales through the mouthpiece into the chamber with the breath exiting into the breath measuring bag (not shown). In the presence of the tested-for substance in the breath of the subject, the indicator material changes color.

Figure 2:
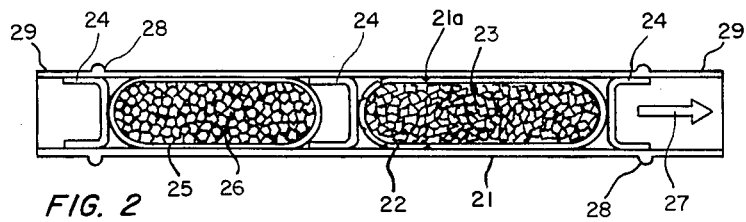
FIG. 2 shows another embodiment of the instant invention wherein a vessel and a fluid retention means are utilized in a single unit.

FIG. 2 depicts another embodiment wherein the testing unit 10 comprises deformable housing 21 containing rupturable vessel 22 with one end having scores 21a to make that end of the vessel substantially more frangible than the remainder of the vessel. Vessel 22 contains cobalt chloride reagent granules and is positioned on one end by clips 24. Vessel 25 contains permanganate chloride reagent granules 26. Arrow 27 points in the desired direction of fluid flow through the test chamber formed in housing 21. Protuberances 28 just medial to cartridge ends 29 position test accessories and test instruments.

Figure 3:
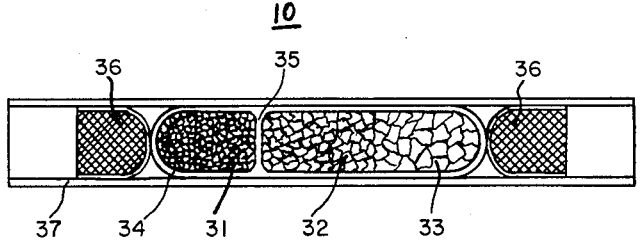
FIG. 3 shows a further embodiment utilizing multiple reagents in a single capsule.

FIG. 3 depicts a further embodiment of testing unit 10 wherein a granular or crystalline reagent 31, glass grit 32, and an additional granular reagent 33 are incorporated into a single receptacle vessel 34. Reagent 31 and glass grit 32 are separated by glass partition 35. Stainless steel positioners 36 position rupturable vessel 34 within housing 37. Partition 35 and the adjacent end of housing 37 can be cooled during the sealing process at a different rate to create stresses sufficient to make the end and seal frangible if the remainder of the vessel is to be used as a liquid retention vessel to form at least a portion of the test chamber.

FIGS. 4 and 5 depict a pregnancy test kit adapted for two tests. FIG. 5 is an enlargement of the test unit of FIG. 4 and utilizes the same number series to the extent possible. The kit of FIG. 4 is made up of a base 41 with cover (not shown) attachment 41a and a mirror 42 angled to display the lower half of the unit when the tube is placed in rack 46. Unit 43 has a funnel-like mouth 44 which is sealed by polyethylene stopper 45. The base 41 with cover attachment 41a supports a tube rack 46 with holes 47 sized to support eyedroppers 48, and units 43. One test unit 43 is shown with stopper 45 removed and the eyedropper 48 having a drop of test fluid (urine) 49 positioned to fall into unit 43 approximately equal to the volume of buffer 50 in the capsule 51. The glass fragments of capsule 51 are shown resting on porous support 52; mirror images 43a and 48a are shown on mirror 42. In operation, the capsule 51 is ruptured, allowing the buffer solution 50 to flow onto the reagent tablet 54. The test fluid 40 flows through the crushed vessel 50 and filter 52 into lower test chamber 53. Stopper 45 and lower test chamber 53 are fitted into unit 43 and covered tightly enough to form a substantially hermetically sealed unit.

In the test of FIG. 4, a tablet 54 of, for example, hCG on sheep erythrocytes and a tablet of, for example, hGC antiserum are placed in an open-ended lower test receptacle 53. Lower test receptacle 53 is not rupturable and presses against the housing wall of unit 43 in sufficient proximity to form a seal which prevents loss of fluid. The appearance of a ring in the fluid mixture of cartridge 43 after 1–3 hours waiting indicates pregnancy. This process is generally taught in U.S. Pat. No. 3,655,838.

FIG. 6 depicts a breath analysis test kit with five receptacles 55 supported in wells 56 and in base 57. A breath volume bag 58 is shown rolled up and inserted in slot 59. Transparent tape closures 60 with lift tab 61 are shown covering five wells 62 containing mouthpieces (not shown) (see FIG. 1). Attachment devices 63 hold a cover (not shown) in place when positioned on the test kit.

BEST MODE FOR PRACTICING THE INVENTION

The detection devices in accordance with this invention have many applications for differing types of tests and test equipment. The device can be used to detect predetermined chemical concentrations of indicated substances in fluids which include both liquids and gases. The indicator material can comprise more than one substance and can be contained in a single capsule or within separate capsules. The housings which form the test chamber may be a pre-manufactured single disposable unit or can be a part of a kit which, for example, can contain many sealed rupturable capsules of indicator reagent which are insertable into the housing to test for more than one substance, as for example, detecting the presence of drug use. The deformable housing or casing which may be used in accordance with the invention are preferably tubular in shape but may be of any size or dimension which forms a receptacle for the rupturable vessels and a test chamber suitable in size to contain the reagent, the fractured vessel particles and the fluid to be tested.

In order to determine visible changes such as color, texture or the like, the housing must be transparent or at least translucent. One can envision, however, indicators which would change, for example, temperature or conductivity in the presence of the substance being tested for. In that case, the housing would not necessarily have to be transparent or translucent.

The deformable character of the housing or casing presupposes some elasticity so that the housing returns to substantially its prior shape to provide sufficient volume to form the test chamber. Likewise, the entire housing need not be deformable (as shown in FIG. 5). Only that portion of the housing proximate the reagent containing vessel need have sufficient deformability to convey sufficient pressure to the rupturable vessel.

Likewise, the housing must provide a test chamber of integrity when subjected to the reagent(s), sample fluid and any interaction of the two. Thus, the housing must be substantially impermeable to and insoluble in such substances, as well as substantially impermeable to ambient environment.

A material which can be used for the housing is any deformable substance which will allow sufficient pressure and/or force to be applied through the wall of the housing to fracture the reagent containing vessel or capsule inside while having sufficient thickness and resistivity to avoid being punctured by random pressures from outside the housing as well as from glass fragments from the ruptured vessel. Normally, the housing is of a plastic tubing such as, for example, polyvinyl chloride, a neoprene, polyester, or other inert, transparent or translucent flexible tubing of desired diameter. An exemplary tubing would have a diameter of approximately ⅜" and would be relatively thin-walled, i.e., in the range of from 1/32" to 1/64" thickness. The tubing may be flared at the entry end to form a funnel for urine and other liquid test fluids.

In accordance with the instant invention, the reagent material is contained in a sealed, rupturable vessel within the housing. Preferably, the vessel will have an external diameter just slightly less than, or about the same as, the internal diameter of the deformable casing. The rupturable capsule is substantially inert to and insoluble in the test fluid, reagent(s) and the ambient environment. The vessel must be capable of containing a solid, liquid or gaseous reagent and is preferably of thin-walled construction. Suitable materials include glass, plastic and the like. In one embodiment, the vessel wall contains a non-penetrating "score" on the wall to provide a pressure point about which the vessel wall will rupture. The vessel(s) may be segmented and/or compartmentalized through the use of, for example, dividers to separate the reagents, which dividers can be porous or non-porous. Pressure on the center of the preferred thin-walled glass vessel sufficient to rupture the walls of the vessel usually suffices to shatter the vessel to the extent that no further breakage is required for a complete interaction between the test fluid and the reagent. Glass partitions such as those shown in FIG. 3 and an adjacent end may be stressed during anealing so that only the stressed or scored portion is frangible, leaving the remaining portion of the vessel to act as a receptacle or container which forms the test chamber within the housing.

The vessels or capsules which can be utilized include sealed ampules and ampules having an open end upon which a membrane is mechanically placed in manufacture for reagents which are heat sensitive.

Wadding or filter material can be fastened to the inner wall of the housing to provide a filter through which breath or the like can be passed to reduce dirt and particle displacement and prevent the indicator material from being blown out of the chamber. The filter may also provide a stationing or positioning means for the sealed reagent-containing vessel(s). The filters can be of single unit construction such as a manufactured insert or the like.

The reagents which comprise the indicator material, or a mixture of materials which, when combined in the testing chamber are of an indicator nature, and be doped on a substrate or permeated into a porous substrate for release in the presence of a second solvent. It will be apparent to the skilled artisan that a number of permutations and combinations of reagents, solvents, substrates and the like can be configured proximate the test chamber in one or more vessels for single or sequential release to provide an integral, self-contained, disposable unit having a myriad of applications.

The reagent can be absorbed into the pores of a solid, for example, as taught by the Luckey reference. Alternately the reagent can be granular solid or powdered compounds; singles or mixtures of chemicals; or enzymes or catalysts deposited on a substrate. In one ampule, the reagent, solvent, buffer solution, etc. can be a liquid and in another, dry. As indicated above, single or multiple reagents, reactants, catalysts, or solvents can be used.

One of the preferred utilities for detection devices of this invention is in the testing of exhaled breath to indicate blood alcohol content. Another preferred use tests for urine glucose. In such a test, a dry reagent is made up of glucose oxidase (1.3 I.U.), horseradish peroxidase (3200 I.U.), a buffer and inerts. A negative reaction provides an aqua coloration trending through light green for a 0.1% concentration; a brownish green for a 0.5% concentration; and a dark brown for 2 or more percent concentration. This test is generally taught in U.S. Pat. No. 3,814,668.

In still another test, urine pH can be tested with phenapthazine granules contained in a reagent vessel. The fluid mixture is retained by a test chamber receptacle. The color yellow indicates a pH of 4.5; green a pH of 6; and purple a pH of 7.5.

In still another test, the ketone content of blood serum, plasma, or whole blood is determined using a reagent made up of 1 part nitroprusside and 9 parts glycine. The granules in the vessel also contain alkaline buffer, filler and binder. The reagent is poured through the test unit to obtain a deep blue to purple color signifying the presence of ketones.

The presence of hydrogen sulfide in a gas stream is determined in a two-vessel containing modification of FIG. 2 wherein an aqueous acid solution is contained in the upstream receptacle vessel and solid lead acetate granules are contained in the downstream vessel. The tube can be positioned on its bottom and/or the end can be placed over a post which forces it to remain upright. A black color signifies the presence of hydrogen sulfide.

In still another embodiment, the amount of the vitamin thiamine is determined in a cartridge made up of an upstream ampule containing an aqueous alkaline solution and a receptacle forming the test chamber containing reagent granules of p-amino acetophenone. After the upstream ampule and the upper end of the downstream ampule are broken (See FIG. 2), urine is inserted into the device. A red pigment in the bottom ampule denotes the presence and concentration of thiamine.

Further embodiments of the instant invention employ, for example, housings or casings or tubes which contain flared ends. Further, as indicated in FIGS. 1 and 2, accessories can be added. Accessories include mouthpieces, funnels, bases to hold the devices in a vertical or other particular position, breath or other gas flow or volume controls, etc. As indicated in FIGS. 1 and 2, the positioning of the accessories can be accomplished by ridges on the housing or by the configuration of the accessories themselves. Where a seal is required, accessories such as an eyedropper can also be designed to act as sealant means for the device during the test.

In accordance with a further aspect of the instant invention, test instruments can be used in conjunction with the instant test device to accurately determine, for example, color change, precipitant volume, or the like. Test instruments can also be used to record data or merely to more accurately quantify the results. Alternately, the cartridges can be used to prepare a liquid test fluid for assay by a test instrument. Such test instruments can utilized chromatographic, spectrographic, gravimetric, or other standard means to record the specific reuslt. The test instruments can give visual readouts through gauges or other displays, can record the data on any permanent media or input the data into a computer.

The test devices of the instant invention are improvements over the prior art in that there is no possibility of the user being cut by broken or cut tips while maintaining the reagents, solvent solutions, etc., in a sealed condition, thus providing an integral, field-usable, disposable test device containing fresh reagent until use.

While the invention has been explained in relation to a preferred embodiment, it is understood that various modifications thereof will become apparent to those skilled in the art upon reading the specification. The invention is intended to cover such modifications as fall within the scope of the appended claims.

I claim:

1. A portable, disposable device for detecting the presence of a substance in a test fluid by means of contacting a selection of indicator materials which undergo a detectible change in the presence of a predetermined amount of such substance comprising:
    at least one rupturable vessel means for sealably retaining therein said selection of indicator materials wherein at least one of said indicator materials is a solid and wherein said at least one vessel means is substantially inert with respect to and impenetrable by said indicator materials;
    a pliable housing means encasing said at least one vessel means and forming therewithin a test chamber, said pliable housing means having at least one end which terminates at and defines an opening which communicates between the test chamber and the ambient environment for introducing the substance into the chamber for testing wherein said housing means contacts said vessel means and is of sufficient deformability to transfer a rupturing force to said vessel means, and wherein said pliable housing is substantially inert to the indicator materials, the test fluid and the interaction of the substance with said indicator materials and,
    a porous means within said pliable housing adapted to allow communication of the test fluid containing the substance with the indicator materials, while preventing said indicator materials from exiting the test chamber.

2. The device of claim 1 wherein said at least one vessel means is constructed of glass.

3. The device of claim 1 wherein said at least one vessel means is constructed of plastic.

4. The device of claim 1 wherein a portion of said at least one vessel means is substantially more frangible than the remainder of said vessel means.

5. The device of claim 1 wherein said at least one vessel means forms a test receptacle when ruptured.

6. The device of claim 1 wherein said at least one vessel means includes at least one partition means therein effective to separate a portion of said selection of indicator materials.

7. The device of claim 1 having at least two vessel means.

8. The device of claim 7 wherein at least one of said at least two vessel means contains a liquid indicator material.

9. A process for detecting the presence of a substance in a test fluid by means of contacting a selection of indicator materials which undergo a detectible change in the presence of a predetermined amount of such substance, comprising the steps of:
    applying a rupturing force to a pliable housing means having a test chamber and encasingly contacting at least one rupturable vessel means, wherein at least one end of said housing means terminates at and defines an opening which communicates between the test chamber and the ambient environment for introducing said substance into the chamber for testing and contains at least one porous means to allow communication of the test fluid with said indicator materials, yet prevent said indicator material from exiting the test chamber, and is of sufficient deformability to transfer said rupturing force to said at least one vessel and is substantially inert to said indicator materials, the test fluid and the interaction of the fluid to be tested with said indicator materials, said applied rupturing force being effective to rupture said at least one of rupturable vessel means which sealably retains therein said indicator materials wherein at least one of said indicator is a solid and, wherein said vessel is substantially inert with respect to and impenetrable by said indicator materials; and
    passing a fluid into said test chamber to contact said at least one indicator material in order to determine the presence of the substance being tested for.

10. A test kit for detecting various substances in a test fluid by means of contacting a selection of indicator materials which undergo a detectible change in the presence of a predetermined amount of such substances, comprising
    at least one rupturable vessel means for sealably retaining therein said indicator materials wherein at least one of said indicator materials is a solid and wherein said at least one vessel means is substantially inert with respect to and impenetrable by said indicator materials, wherein said at least one vessel means is able of insertion into a pliable housing means;
    a pliable housing means forming therewithin a test chamber, said pliable housing means having at least one end which terminates at and defines an opening which communicates between the test chamber and the ambient environment for introducing said substances into the chamber for testing and being capable of encasingly contacting said at least one vessle therein upon insertion, wherein said pliable housing means is of sufficient deformability to transfer a rupturing force to said at least one vessel, and wherein said pliable housing is substantially inert to said indicator materials, the test fluid and the interaction of the test fluid with said indicator materials; and, a porous means contained within said pliable housing means for allowing communication of the test fluid with said indicator materials, yet prevent said indicator materials from exiting the test chamber.

* * * * *